Aug. 30, 1938. H. HOFMANN Plant Pat. 286
ROSE
Filed March 26, 1937
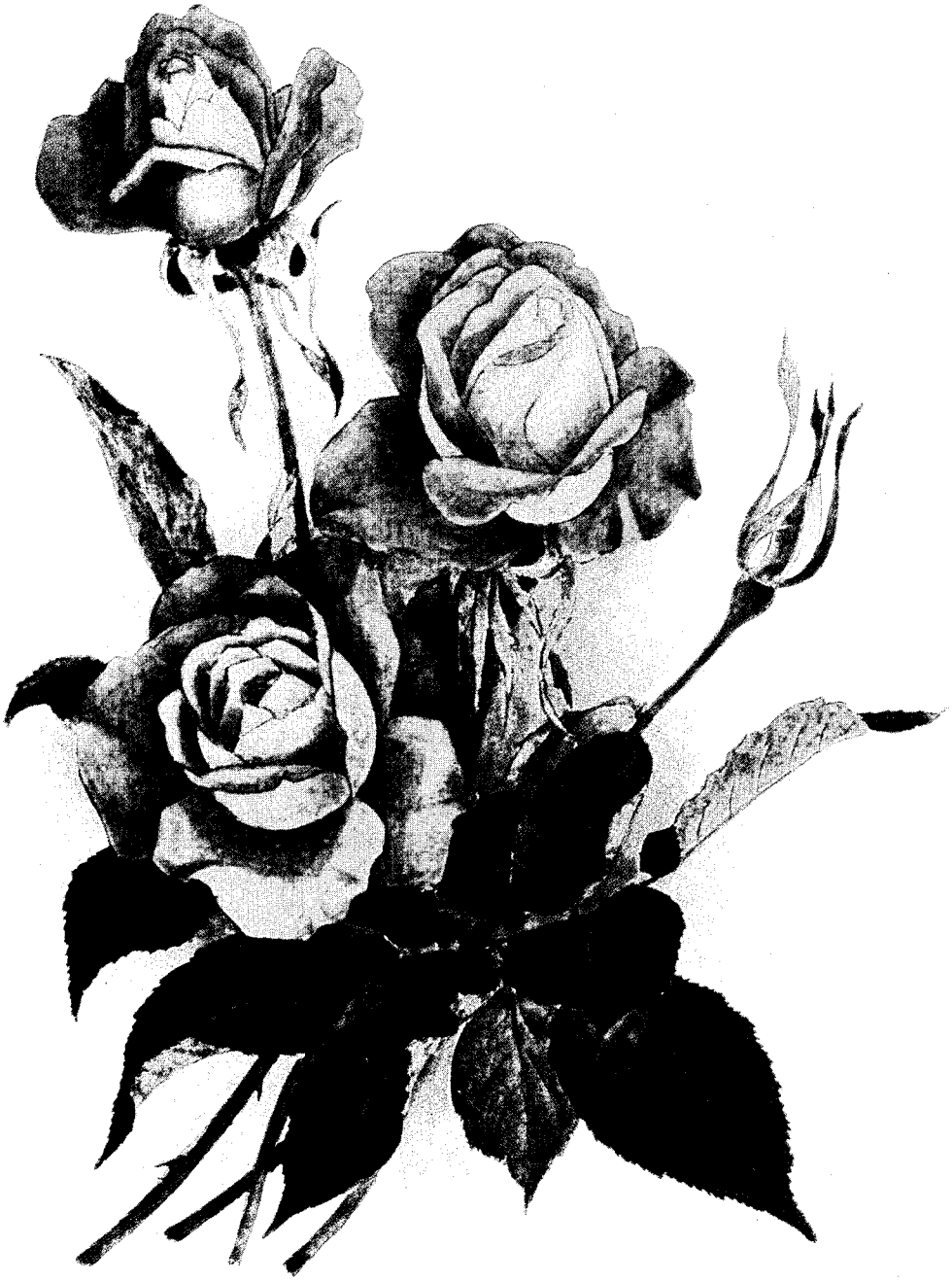
Witness
Addison E. Avery
Inventor
Harry Hofmann
By: Rummler Rummler & Woodworth
Attys.

Patented Aug. 30, 1938

Plant Pat. 286

UNITED STATES PATENT OFFICE

286

ROSE

Harry Hofmann, Jacksonville, Ill.

Application March 26, 1937, Serial No. 133,210

1 Claim. (Cl. 47—61)

The new rose which may be identified by the accompanying illustration and the following description is a mutational variant occurring on one of the plants of the rose known as "Better Times", Plant Patent No. 23.

The improved rose to which this application relates was discovered about two years prior to the application and since then has been developed by taking scions from a branch of the original variant mutant and grafting the scions onto foreign wood and then throughout the period of approximately eighteen months with this method of continuous reproduction of the rose, it has remained consistently true to form and color, substantially as illustrated.

The most conspicuous characteristics of the new rose are its consistent uniformity in form, depth of warm color (Carmine Ridgway, Plate 1—1R—Line *i*) and size, and with foliage of a dark shade of green. The foliage is smaller and darker than in the parent plant. The underside of the leaves and the underside of the tips of the sepals are a slate-violet in general color. The sepals are longer than average. The flower opens curly to some extent and averages about 4 inches in diameter, and the stems bear garnet colored thorns.

The colors of this rose in detail are as follows: Body of the flower and petals thereof, Carmine, Plate 1—1R—Line *i*, found in Color Standards and Color Nomenclature by Robert Ridgway.

The above-mentioned Carmine is somewhat darker than the nearest approach found to this rose color in Maerz and Paul "A Dictionary of Color", Plate 1—L—1.

The petals shade into and reflect in the deepest shadows a color which may be found in the "Rose Manual" of J. H. Nichols, Garnet, Plate 4 Red Range 2.

Maerz and Paul's Color Dictionary is referred to for the remaining colors mentioned below:

| | Color | Plate | Letter | No. |
|---|---|---|---|---|
| Base of petal | Cerise | 4 | J | 6 |
| Body of leaf | A shade of Green | 24 | L | 10 |
| Underside of leaf close to ribs. | Smoke Grey+ | 28 | A | 2 |
| Shading into body of under leaf. | Slate-Violet | 6 | I | 8 |
| Main under rib | Garnet+ | 7 | J | 6 |
| Calyx | A shade of Green | 21 | L | 8 |
| Inside of sepals | Water Green | 19 | C | 2 |
| Back of sepals | A shade of Green | 21 | L | 8 |
| Stems shading from calyx color to. | Holly Green | 23 | L | 1 |
| Thorns | Garnet+ | 7 | J | 6 |
| Bottom of inside of sepal tips same as under leaf. | Slate-Violet | 6 | I | 8 |

Aside from the above-mentioned color combination and uniformity in size and color, the blossoms have decidedly good keeping qualities as to color and form on the plant and when cut, and the plant may be otherwise distinguished by the following characteristics:

*Parentage.*—Sport of "Better Times".

*Blooming habit.*—(Observations made in greenhouse at Jacksonville, Illinois) continuous.

*Bud.*—Size, large.

*Form.*—Long. Is not affected by wet weather. Is not affected by dry weather.

*Color.*—When sepals first divide—Carmine. When petals begin to unfold—Carmine. When half blown: inside of petals, Carmine; reverse of petals, same (Plate 1—1R—Line *i*, Ridgway's Color Standards and Color Nomenclature).

*Sepals.*—Curl back.

*Calyx.*—Funnel-shape, long and smooth.

*Peduncle.*—Long.

*Aspect.*—Prickly.

*Strength.*—Stiff.

*Opening.*—Bud opens well. Not affected by adverse conditions.

*Bloom.*—Medium average size when fully expanded.

*Stems.*—Long and strong.

*Form.*—High.

*Petalage.*—Very double, many petals, 28 petals normal.

*Discoloration.*—First day—none. Second day—none. Third day—none. Kept in Frigidaire 8 days—holding its color.

*Texture.*—Thick.

*Appearance.*—Outside—shiny and velvety. Inside—shiny and velvety.

*Fragrance.*—Slight (pleasant).

*Lastingness.*—On the plant—very long. As a cut flower—very long.

The blossoms of this rose plant have a greater intensity of color, are darker and richer, and are more uniformly symmetrical than are the blossoms of the parent plant and the stems have more and larger thorns than the parent. There is a conspicuous difference in color on the upper and lower sides of the leaves, the upper side being of a deeper shade of green than the parent plant and the under side having a more slate-violet to grey tone.

I claim:

A variety of rose plant as above described in which the bloom is of substantially uniform, deep carmine, consistently regular in form with petals somewhat crinkled at their outer edges; stems bearing a few garnet-colored thorns; sepals water-green on the inside except the tips which are a slate-violet color; and having foliage of a dark shade of green on the upper side of the leaves and of a slate-violet color underneath shading toward the main leaf rib to smoke-grey.

HARRY HOFMANN.